US011257581B2

(12) United States Patent
Nikolova-Simons et al.

(10) Patent No.: US 11,257,581 B2
(45) Date of Patent: Feb. 22, 2022

(54) SYSTEM AND METHOD FOR COMPUTERIZED VISUAL DISPLAY OF USER COMPLIANCE WITH A CARE PLAN

(71) Applicant: KONINKLIJKE PHILIPS N.V., Eindhoven (NL)

(72) Inventors: Mariana Nikolova-Simons, Eindhoven (NL); Dieter Maria Alfons Van De Craen, Balen (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/600,692

(22) Filed: Oct. 14, 2019

(65) Prior Publication Data
US 2020/0043601 A1 Feb. 6, 2020

Related U.S. Application Data

(63) Continuation of application No. 14/458,899, filed on Aug. 13, 2014, now abandoned.
(Continued)

(51) Int. Cl.
G09B 19/00 (2006.01)
G16H 20/30 (2018.01)
(Continued)

(52) U.S. Cl.
CPC ............ *G16H 20/30* (2018.01); *G16H 30/20* (2018.01); *G16H 20/60* (2018.01); *G16H 20/70* (2018.01)

(58) Field of Classification Search
CPC ........ G16H 40/67; G16H 10/60; G16H 20/30; G16H 20/60; G16H 40/63; G16H 15/00; G16H 20/10; G16H 50/20; G16H 50/30; G16H 80/00; G16H 10/20; G16H 30/40; G16H 40/20; G16H 10/65; G16H 20/40; G16H 20/70; G16H 30/00; G16H 40/00; G16H 40/60; G16H 10/40; G16H 50/70; G06Q 30/02; G06Q 10/10; G06Q 50/01; G06Q 30/0241; G06Q 30/0279;
(Continued)

(56) References Cited

U.S. PATENT DOCUMENTS 6,802,810 B2 10/2004 Ciarniello et al.
2007/0033072 A1 2/2007 Bildirici
(Continued)

FOREIGN PATENT DOCUMENTS

JP 2006146410 A 6/2006
RU 2010110773 A 9/2011
(Continued)

*Primary Examiner* — Maroun P Kanaan

(57) ABSTRACT

A display having different segments that correspond to different categories of a care plan for a user may be provided. A dimension for the display segment is determined. The dimension indicates a relative importance of a care plan category that corresponds to the display segment compared to other care plan categories. A brightness is determined for the display segment based on the user's compliance with the care for the care plan category that corresponds to the display segment. The display segment is overlaid over at least a portion of a user-selected image for the display segment. A configuration of the overlay is based on the determined dimension and the determined brightness.

19 Claims, 6 Drawing Sheets

Related U.S. Application Data

(60) Provisional application No. 61/866,100, filed on Aug. 15, 2013.

(51) Int. Cl.
*G16H 30/20* (2018.01)
*G16H 20/60* (2018.01)
*G16H 20/70* (2018.01)

(58) Field of Classification Search
CPC ...... G06Q 30/00; G06Q 10/06; G06Q 10/087; G06Q 30/0643; G06Q 40/00; G06Q 40/04; G06F 40/40; G06F 16/24578; G06F 16/951; G06F 11/3065
See application file for complete search history.

(56) References Cited

U.S. PATENT DOCUMENTS

| | | | |
|---|---|---|---|
| 2011/0153350 A1 | 6/2011 | Simons-Nikolova et al. | |
| 2013/0094831 A1* | 4/2013 | Suzuki | G11B 27/34 386/230 |
| 2013/0317840 A1* | 11/2013 | Creswell | G16H 10/60 705/2 |
| 2014/0067421 A1* | 3/2014 | Bernstein | A61B 5/1473 705/3 |
| 2016/0055758 A1* | 2/2016 | Francis | G16H 50/30 434/236 |

FOREIGN PATENT DOCUMENTS

| | | |
|---|---|---|
| WO | 2011039676 A2 | 4/2011 |
| WO | 2011054004 A1 | 5/2011 |

\* cited by examiner

| | Mon | Tue | Wed | Thu | Fri | Sat | Sun |
|---|---|---|---|---|---|---|---|
| week 1: Physiological | Signs & Symptoms 1 | Signs & Symptoms 2 | Medications overview 1 | Medications overview 2 | Medications compliance | | |
| week 2: Emotional | Emotional well-being | Stress | Depression 1 | Depression 2 | Anxiety | | |
| week 3: Nutritional | Nutrition 1 | Nutrition 2 | Nutrition 3 | Healthy weight 1 | Healthy weight 2 | | |
| week 4: Social | Social support | Travel checklist | Family & Friends, Part 1 | Family & Friends, Part 2 | Family & Friends, Part 3 | | |

FIG. 7

SYSTEM AND METHOD FOR COMPUTERIZED VISUAL DISPLAY OF USER COMPLIANCE WITH A CARE PLAN

RELATED APPLICATIONS

This application is a continuation of U.S. patent application Ser. No. 14/458,899, filed Aug. 13, 2014, which claims the benefits of U.S. Provisional Application No. 61/866,100, each of which is incorporated herein by reference in its entirety.

FIELD OF THE INVENTION

The present application relates to computerized visual display of user compliance with a care plan.

BACKGROUND OF THE INVENTION

Chronic conditions such as heart failure (HF) place a tremendous strain on patients, their families, the community, and the health care system because there are no real "cures". Approximately 5.8 million Americans are living with HF, with an estimated incidence of 660,000 new cases each year. Further, worsening of HF is a leading cause of readmission within 30 days post-discharge across all diseases, e.g., every 1 out of 4 patients is going back to the hospital in the 30 days post-discharge period.

Patient's non-compliance to chronic conditions therapy specified by a care plan (CP; generally being a specification of a coaching intervention) decreases the care plan efficacy and exposes the patient to clinical destabilization, which can lead to exacerbating disease symptoms. Evidence from clinical trials and validated patient's and clinician's insights show that the most commonly identified cause of disease worsening, e.g. Heart Failure decompensation is non-compliance with medication, low sodium diet, fluid restriction and physical activity. Non-compliance is the precipitating factor of exacerbation. Hence, patient's compliance to a care plan is a prerequisite for better clinical outcomes, e.g., reduced readmissions and mortality.

The care plan in home settings is usually presented to the patients via a telehealth system. The telehealth system can be a stand-alone service or an embedded service in a patient portal which supports patients with personalized information and tools to improve their understanding of their chronic condition(s) and the benefits of compliance with their care plan.

SUMMARY OF THE INVENTION

Aspects of the present invention are related to providing a computerized visual display of user compliance with a care plan. The computerized visual display is configured to better motivate and compliance by the user to the plan, and enable dynamic changes to the plan even when the plan is being executed by the user.

A display having different segments that correspond to different categories of a care plan for a user may be provided. A dimension for the display segment is determined. The dimension indicates a relative importance of a care plan category that corresponds to the display segment compared to other care plan categories. A brightness is determined for the display segment based on the user's compliance with the care for the care plan category that corresponds to the display segment. The display segment is overlaid over at least a portion of a user-selected image for the display segment. A configuration of the overlay is based on the determined dimension and the determined brightness. Advantageously, the size, shape, etc. (e.g., a dimension) of a segment may indicate an importance of a particular segment and corresponding care plan category relative to other segments and care plan goals categories. Further, the color, brightness, etc. of each segment may represent the progress a user makes toward completing care plan requirements for a particular category associated with a given segment. Thus, the display segments provide a fast and easy to understand overview interpretation of a user's progress toward care plan goals.

Embodiments of the invention are defined in the claims. It shall be understood that the claimed method and medium have similar and/or identical embodiments as the claimed system and as defined in the claims.

The present invention is based on the idea to take explicitly the user's life goals into account during the creation of a personalized care plan by influencing the care plan design on a user base. In other words, the user's defined life goals, i.e. what users really care about, are translated into care plan health goals. Achieving motivation and compliance to the care plan and underlying health goals with the improved display system and method described herein improves prior known healthcare telehealth systems.

Further, based on the information displayed, and the way the information is displayed by the present improved system and method, the care plan can be dynamically changed, e.g. by a care plan engine which creates and executes the care plan, at run time once it is at the execution phase since the proposed healthcare system and method do generally not refer to a static care plan library that consists of a set of pre-defined care plans with embedded health goals that have been reviewed and approved to comply with all applicable guidelines and clinical standards.

Thus, in summary, the proposed healthcare system and method are able to generate care plans with different specifications per user covering the users' variety of life goals.

In this context, life goals generally touch on the things that are most important to users in their live, the things that they care about the most. For example, a HF user might express his life goals as "being able to play with grandchildren without being fatigue after 5 min", "being able to work in the garden without getting breathlessness" or "being able to vacuum clean my house without needing to rest twice".

Health goals, in contrast, are the choices and lifestyle behavior that people can pursue in order to address their most important health issues. For example, typical HF user's health goals are medication adherence, symptoms worsening monitoring, low sodium diet, fluid restriction and regular physical activity.

Focusing on user's life goal creates motivation and energy that can prompt real behavioral change needed to drive the compliance to the care plan expressed by achieving the health goals. The present invention focuses on the translation of user's defined life goals into a personalized (user-driven) care plan and its underlying health goals. In some embodiments, a reverse translation is provided as well to provide user feedback and tracking of the user's compliance.

BRIEF DESCRIPTION OF THE DRAWINGS

These and other aspects of the invention will be apparent from and elucidated with reference to the embodiment(s) described hereinafter. In the following drawings FIG. 7 shows a diagram of an exemplary care plan specification.

DETAILED DESCRIPTION OF THE INVENTION

Figure 1:
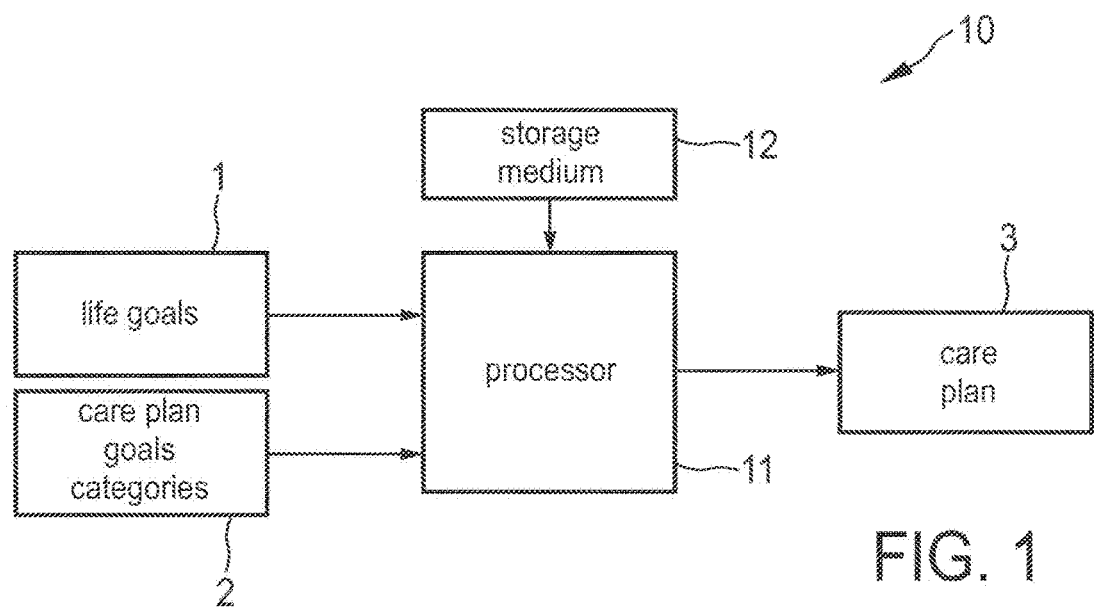
FIG. 1 shows a schematic diagram of a first embodiment of a healthcare system according to the present invention.
Figure 2:
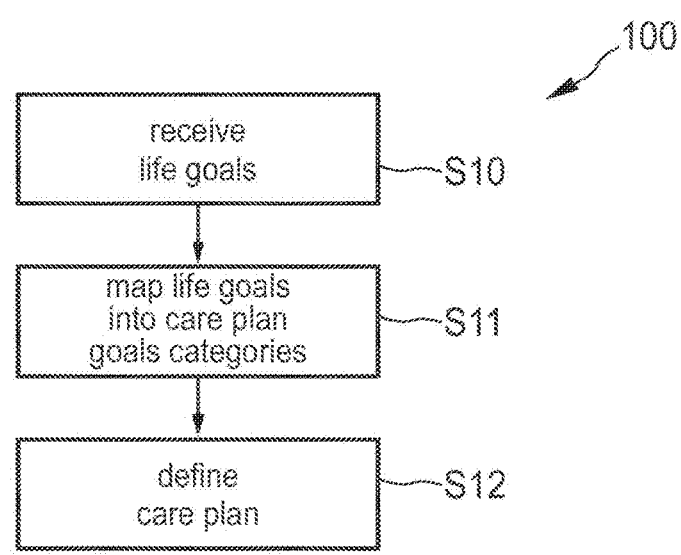
FIG. 2 shows a schematic diagram of a first embodiment of a healthcare method according to the present invention.

FIG. 1 shows a schematic diagram of a first embodiment of a healthcare system 10 according to the present invention for creating a personalized care plan for a user (e.g. a patient; in the following reference will be made to patient, but this may generally be understood as a user). It comprises a processor 11 and a computer-readable storage medium 12. The computer-readable storage medium 12 contains instructions for execution by the processor 11. These instructions cause the processor 11 to perform the steps of a healthcare method 100 as illustrated in the flow chart shown in FIG. 2.

In a first step S10 life goal information 1 defined by a user is received, said life goal information indicating the user's life goals. In a second step S11 the received life goal information 1 is mapped into care plan goals categories 2 including two or more categories. In a third step S12 a care plan is defined, said care plan including a care plan schedule for the care plan goals categories 2 into which the received life goal information 1 has been mapped. Said schedule includes, per care plan goals category, one or more care plan content elements representing elements of the care plan and, preferably, time information representing the duration and/or time of executing said care plan content elements.

In the context of the present invention life goals are generally defined by the patients (users) and not by the medical professionals for the purpose of describing the internal patient's motivators (i.e. what matters to the patients) in order to adhere to a medical treatment. Life goals are input for tailored design of a medical treatment specified by a care plan rather than measurements (like quality-of-life parameters) for the effectiveness of a medical treatment. Such quality-of-life measurements/parameters are usually defined by medical professionals/scientists for the purpose of measuring the effectiveness of a medical treatment. For instance, such quality-of-life parameters are used a (long-term) disease management program that uses technology solutions such as a patient monitoring and management system with a comprehensive care or in a medication management program that uses technology solutions for behaviors change.

The proposed healthcare system provides a personalized care plan. Patient A with life goals A and patient B with life goals B (different from life goals A) will get as an output of the proposed system:

personalized care plans A and B, respectively, with different structure based on the mapping of life goals to care plan goals which is different for A and B; and in a preferred embodiment, personalized feedback on their progress to life goals A and B, respectively, based on the actual tracking of care plan goals and their reverse mapping to life goals.

Figure 3:
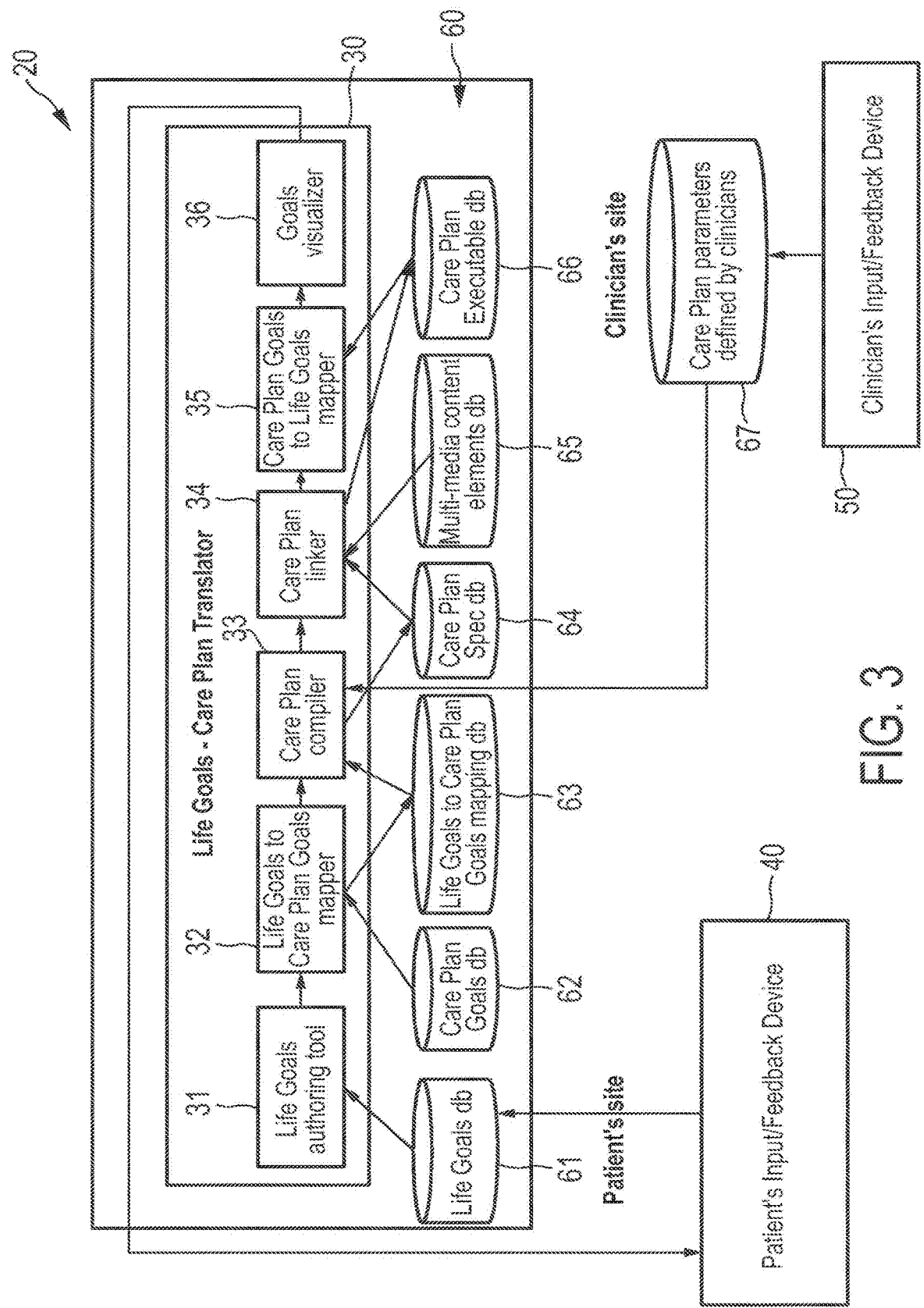
FIG. 3 shows a schematic diagram of a second, more detailed embodiment of a healthcare system according to the present invention.
Figure 4:
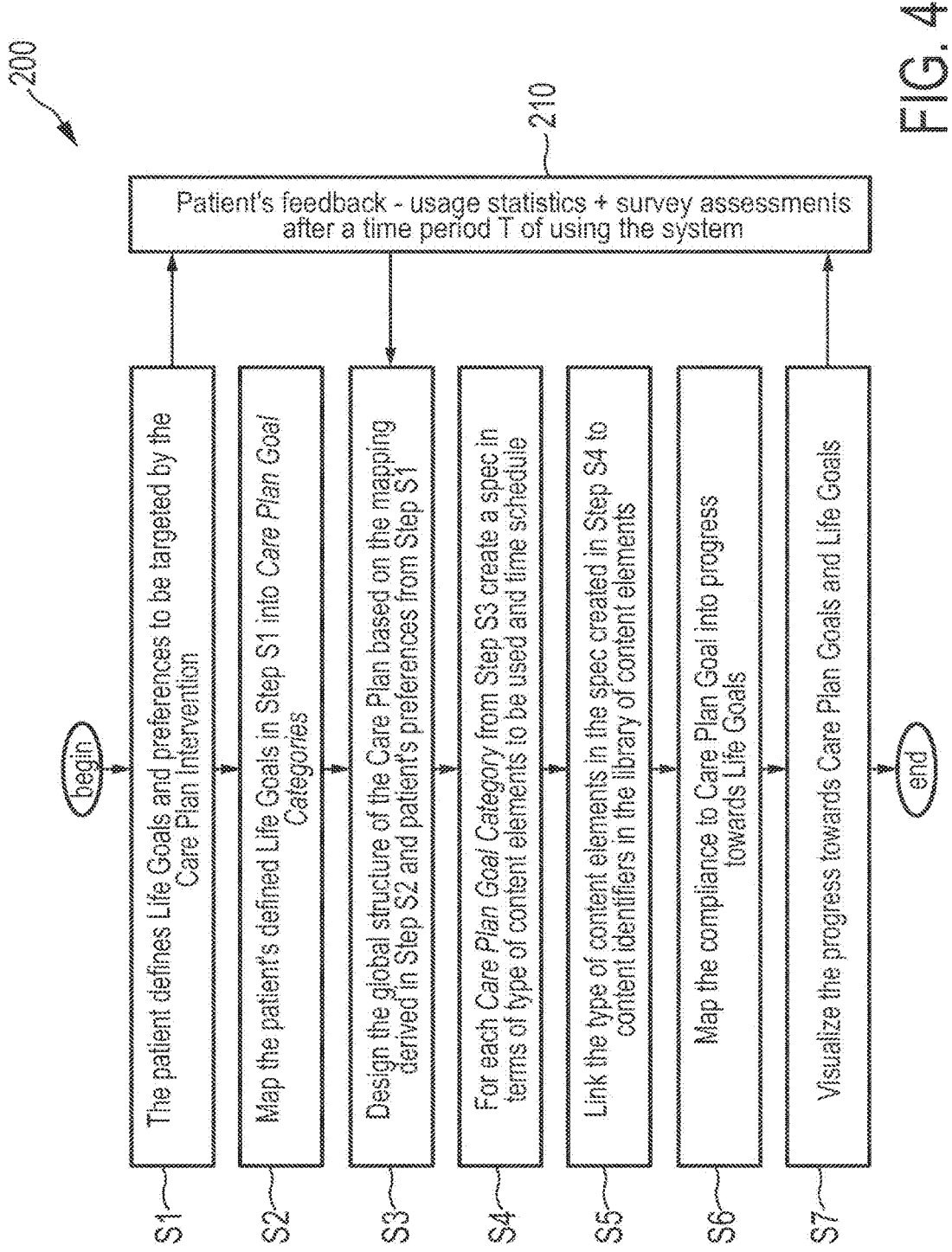
FIG. 4 shows a schematic diagram of a second embodiment of a healthcare method according to the present invention.

FIG. 3 shows a schematic diagram of a second, more detailed embodiment of a healthcare system 20 according to the present invention, and FIG. 4 shows a schematic diagram of a second embodiment of a healthcare method 200 according to the present invention, by way of which more details of the present invention will be explained hereinafter.

The healthcare system 20 comprises a Life Goals-Care Plan Translator 30, which carries out the steps of the healthcare method 200 and which may be implemented by the processor 11 of the healthcare system 10 shown in FIG. 1. Here in this embodiment the Life Goals-Care Plan Translator 30 is implemented by a back-end clinical server system comprising e.g. a patient management server and a care plan server. Other implementations are, however, possible as well, and the particular way of implementing the system 20 is generally not essential for the present invention.

The Life Goals-Care Plan Translator 30 communicates with a patient's input/feedback device 40 on the patient's side and a clinician's input/feedback device 50 on the clinician's side as well as with various databases 60, which will be explained below in more detail. All these databases may be stored in a common storage, e.g. on a hard disk, or separately in different storage units. They store both predetermined content as well as results of previous steps of the proposed method.

The Life Goals-Care Plan Translator 30 comprises a Life Goals Authoring Tool 31, a Life Goals to Care Plan Goals Mapper 32, a Care Plan Compiler 33, a Care Plan Linker 34, a Care Plan Goals to Life Goals Mapper 35, and a Goals Visualizer 36. These elements 31 to 36 may be implemented on a common processor or on two or more separate processors. Further, they may be implemented as a common software tool or as separate software modules which are coupled together. Still further, they may be implemented through a mixture or hard- and software elements.

The Life Goals Authoring Tool 31 allows the patients to define their own life goals and preferences. The Life Goals Authoring Tool 31 performs step S1 of the method 200 illustrated in FIG. 4.

Although life goals often have an important physiological/physical aspect, they can address a much wider spectrum of the patient's needs. Important other aspects can include emotional, intellectual, social, occupational, spiritual or environmental wellness as outlined by the 7-element model of wellness known e.g. from http://wellness.unl.edu/wellness-model. In an embodiment of the present invention discussed hereinafter an adapted version of it is used for chronically ill patients that comprises the following 6 aspects—physiological/physical, emotional, nutritional, social, spiritual and occupational. These aspects form the care plan goals categories. It should be noted that other models with other care plan goals categories may be used as well leading to a different result of the mapping of life goals to care plan goals categories, but generally allowing the same way of mapping.

Although all these care plan goals categories are important for the patient's wellbeing, they will not all be perceived by the patient as equally important. To address the patient preferences, the Life Goals Authoring Tool 31 preferably requests an input from the patient, e.g. through the patient's input/feedback device 40, in order to identify his personal importance for at least some (preferably all) care plan goals categories.

Summing up, the Life Goals Authoring Tool 31 preferably gathers two main sources of information, both being combined in life goal information. On the one hand the patient's life goals (as indicated in column 1 of Table 1 depicted below) and on the other hand the patient's personal preferences with respect to wellness aspects (column 2 in Table 1). This information may be stored or buffered in a Life Goals database (db) 61 and is passed to the Life Goals to Care Plan Goals Mapper 32 in order to create mapping into Care Plan goals categories.

TABLE 1

Example of patient's life goals and personal preferences

| Patient's life goals | Patient's personal preferences |
|---|---|
| Play (with grandchild/with child/with dog/sport) | Physiological/Physical - rank 1 |
| Do a walking tour of Paris (park, tourist destination) | Emotional - rank 2 |
| Attend major (family/work/friend) event - wedding, graduation, reunion | Nutritional - rank 3 |
| Attend church every Sunday | Social - rank 4 |
| To do things (drive, care for, cook for etc.) for myself | Spiritual - rank 5 |
| Be pain/anxiety/worry/depression free | Occupational - rank 6 |

The Life Goals to Care Plan Goals Mapper 32 is able to map the patient's defined life goals and preferences (i.e. the life goal information) into care plan goals categories as illustrated by the examples in Tables 2 and 3 depicted below. The Life Goals to Care Plan Goals Mapper 32 performs step S2 of the method 200 illustrated in FIG. 4 and uses the following care plan goals categories, which may e.g. be stored in a Care Plan Goals database 62:

Physiological/Physical—vital signs measurements for detection of symptoms worsening, medication compliance, physical exercises;

Emotional—anxiety, depression, happiness, mood;

Nutritional—diet, weight, and habits;

Social—relationships, friendships, support network;

Spiritual—religious, philosophical, belief system;

Occupational—work, intellect, academia, financial.

TABLE 2

Example 1 of mapping from patient's defined life goals into care plan goals categories

| | Mapping | | | | | |
|---|---|---|---|---|---|---|
| | Care plan goals categories | | | | | |
| Patient's life goals | Phys. | Emot. | Nut. | Soc. | Spir. | Occup. |
| Play (with grandchild/with child/with dog/sport) | 11 | 1 | 1 | 5 | 1 | 1 |
| Do a walking tour of Paris (park, tourist destination) | 11 | 1 | 1 | 5 | 1 | 1 |
| Attend major (family/work/friend) event - wedding, graduation, reunion | 9 | 4 | 1 | 4 | 1 | 1 |
| Attend church every Sunday | 6 | 1 | 1 | 1 | 10 | 1 |
| To do things (drive, care for, cook for etc.) for myself | 4 | 4 | 1 | 1 | 1 | 9 |
| Total percentages (100%) | 41% | 11% | 5% | 16% | 14% | 13% |

TABLE 3

Example 2 of mapping from patient's defined life goals into care plan goals categories

| | Mapping | | | | | |
|---|---|---|---|---|---|---|
| | Care plan goals categories | | | | | |
| Patient's life goals | Phys. | Emot. | Nut. | Soc. | Spir. | Occup. |
| Be (pain/anxiety/worry/depression) free | 1 | 10 | 1 | 6 | 1 | 1 |
| Cook meals for his family | 1 | 1 | 10 | 6 | 1 | 1 |
| Support his wife | 1 | 4 | 1 | 4 | 1 | 9 |
| To not be perceived as ill | 1 | 7 | 1 | 7 | 3 | 1 |
| Control the house finances | 1 | 1 | 1 | 1 | 1 | 15 |
| Total percentages (100%) | 5% | 23% | 14% | 24% | 7% | 27% |

The mapping coefficients between the patient's life goals and care plan goals categories in Tables 2 and 3 are provided automatically based on applying techniques such as machine vector learning or cluster analysis on a large patient's database (Life Goals to Care Plan Goals mapping database 63).

The Care Plan Compiler 33 uses the output of the Life Goals to Care Plan Goals Mapper 32 to design the global structure of the care plan and for each care plan goals category creates a specification in terms of types of content elements to be used and time schedule. The Care Plan Compiler 33 performs steps S3 and S4 of the method 200 illustrated in FIG. 4.

Figure 5:
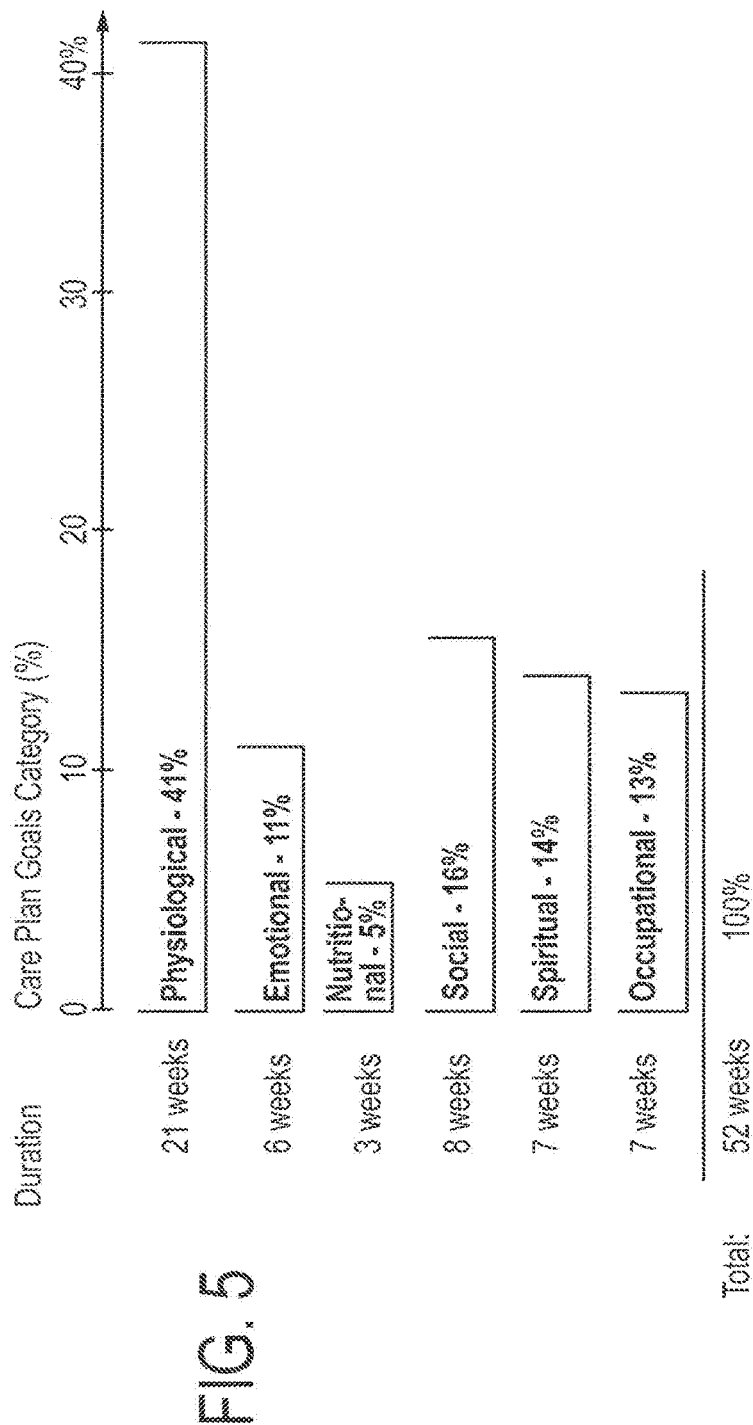
FIG. 5 shows a diagram of an exemplary care plan structure.

The result of step S3 is illustrated in FIG. 5 showing an exemplary care plan structure based on example 1 mapping depicted above in Table 2 and based on care plan duration=1 year (52 weeks) specified in Table 4 and stored in database 67. This value can be overruled by an external source, e.g., total duration of the coaching intervention=duration of a reimbursed intervention, duration required by patient status, duration of a clinical trial, etc. that can be defined by the clinicians and stored in database 67.

Figure 6:
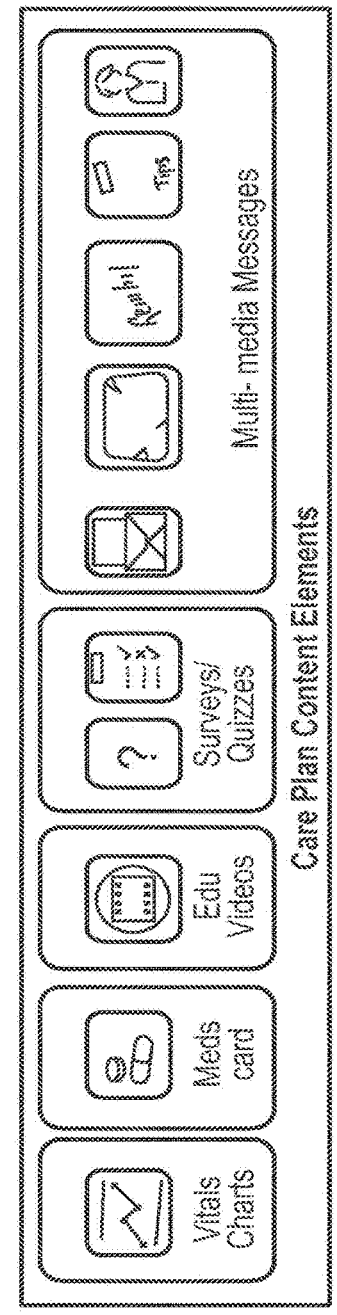
FIG. 6 shows a diagram of types of care plan content elements.

During step S4 the Care Plan Compiler 33 refers to care plan content elements, e.g. to one or more of the multi-media content elements depicted in FIG. 6 and stored in database 65, in order to create the specification for each Care Plan goals category. The content elements can be offered as stand-alone or bundled in a module and may include vital chart, medication (meds) cards, educational (edu) videos, surveys/quizzes and/or multi-media messages. Other content elements may be used as well.

In an embodiment Step S4 has a number of additional input parameters as listed in Table 4 that are mainly defined by the clinicians or caregiver and stored in database 67. These parameters allow for even better personalization of the care plan per patient.

TABLE 4

Default value of the input parameters (the table rows) for each care plan goals category

| Care Plan Goal Categories | Physiological | Emotional | Nutritional | Social | Spiritual | Occupational |
|---|---|---|---|---|---|---|
| Duration | 21 | 6 | 3 | 8 | 7 | 7 |
| Content Elements per goal category | | | | | | |
| Vital Charts | + | | + | | | |
| Medication Card | + | | | | | |
| Edu videos | + | + | + | + | + | + |
| Quizzes/ surveys | + | + | + | + | + | + |
| Multi-media messages | + | + | + | + | + | + |
| Max # of Content Elements | | | | | | |
| per day | 1 | 1 | 1 | 1 | 1 | 1 |
| Care Plan Design Rules | | | | | | |
| Rule 1 | No Content Elements in the weekends | | | | | |
| Rule 2 | A video teaching quiz is scheduled later than the corresponding video | | | | | |
| Rule 3 | A module teaching quiz is scheduled later than the corresponding module | | | | | |
| ... | | | | | | |
| Rule N | Choose a fixed day of the week of a particular content element, e.g., videos every Tuesday | | | | | |

The result of step S4 is a care plan specification that is preferably stored in a care plan specification database 64. An example of a care plan specification is illustrated in FIG. 7 for the first four weeks of the care plan duration taking explicitly into account the patient's personal preferences (see column 2 in Table 1) with respect to care plan goals categories. In this example, a module is scheduled for a patient each week day. A module is a bundle of content elements illustrated in FIG. 6.

The Care Plan Linker 34 establishes a link between the types of content elements in each specification (as e.g. shown in FIG. 7) created by the Care Plan Compiler 33 to content identifiers in the library of content elements stored in a multi-media content elements database 65. If there are different instances of a content element in the content library, e.g., different instances of Sign & Symptoms 1 Module for HD TV and mobile device, then the Care Plan Linker 34 will choose the proper content element instance to link to based on information of the available patient's input/feedback device 40. The Care Plan Linker 34 performs Step S5 of the method 200 illustrated in FIG. 4 and outputs a care plan executable stored in a care plan executable database 66.

The Care Plan Goals to Life Goals Mapper 35 maps patient's compliance to care plan goals into life goals progress. This is step S6 of the method 200 illustrated in FIG. 4. The compliance to the care plan goals categories is e.g. measured with a compliance score as proposed in WO 2011/039676 A2. This document discloses a method of assessing a patient's compliance to an intervention specified by a healthcare professional, the method comprising determining a level of compliance for the patient from interactions between the patient and a remote patient management system. This method for assessing a patient's compliance can be analogously applied here, and the corresponding description of this document is incorporated herein by reference. This method is based on advanced patient-care plan interaction tracking. Physiological parameters collected via measurement devices such as weight scale, blood pressure meter, glucose meter, SpO2 meter, activity monitor, medication dispenser, etc. are used as well as psychological parameters collected via patient-content element interaction tracking.

The compliance score to the care plan goals categories combined with the reverse mapping from Table 2 or Table 3 is preferably used by the Care Plan Goals to Life Goals Mapper 35 to calculate a life goals progress score.

Figure 8:
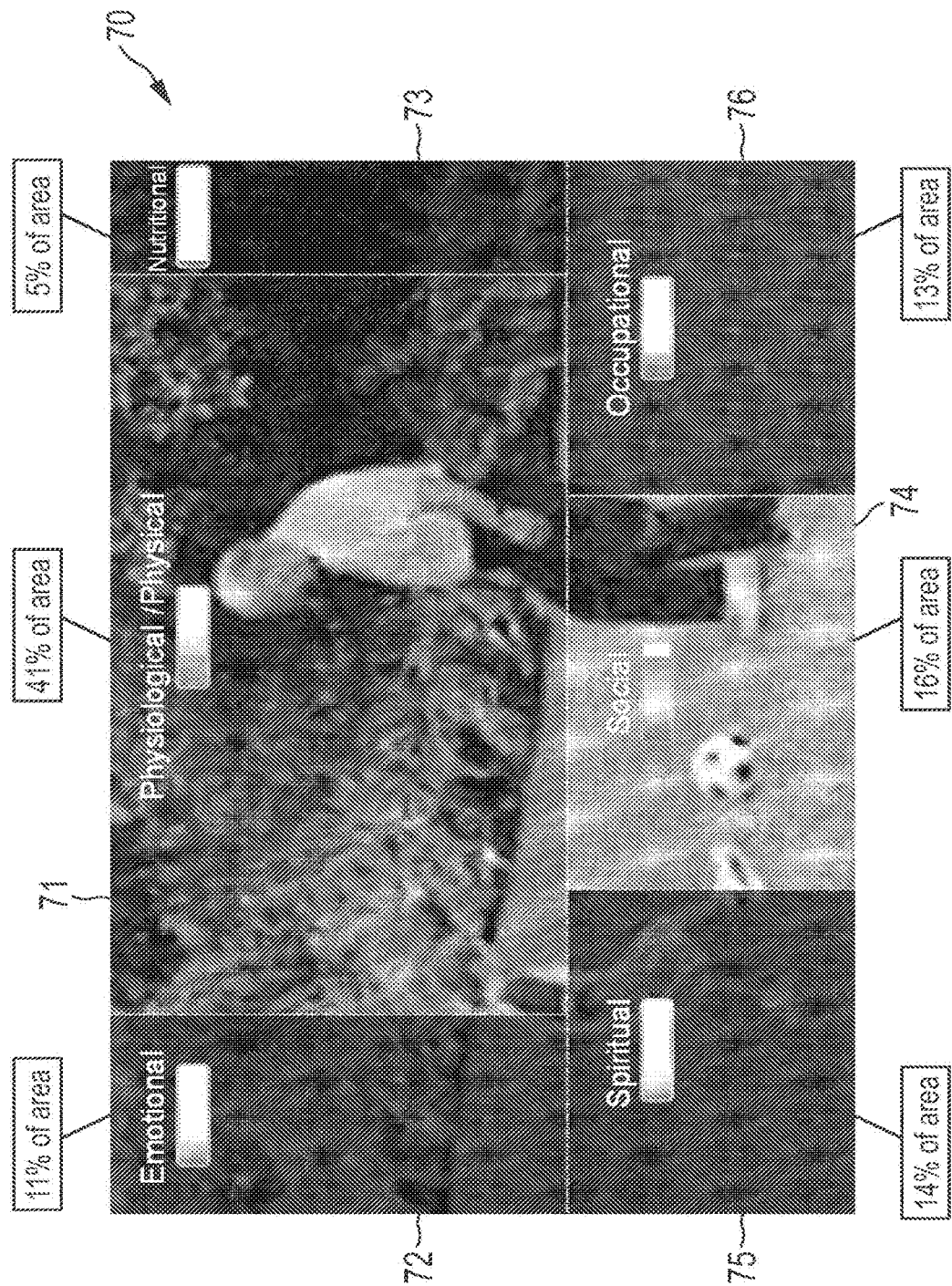
FIG. 8 shows a diagram of an exemplary care plan visualization as dashboard.

The Goals Visualizer 36 visualizes the compliance to care plan goals categories as well as the life goals progress calculated above. This is step S7 of the method 200 illustrated in FIG. 2. The Goals Visualizer 36 offers e.g. a dashboard view to the patient of which an example is given in FIG. 8. The background of the dashboard 70 represents the patient's life goals. The latter are represented by pictures which can be uploaded by the patient or retrieved from a database that contains pictures for the most common life goals.

The dashboard 70 is divided into segments 71, 72, 73, 74, 75, 76 that represent the different care plan goals categories. The size of each segment represents the mapping coefficient between the patient's life goals and the care plan goals category the segment represents. Further, the brightness of each segment represents the progress towards this particular care plan goals category. For example, in FIG. 8 it can be seen that the patient has progressed well on the social category and hence the corresponding segment 74 is bright, while on the other hand the patient has almost made no progress on the nutritional category and as a result the corresponding segment 73 is almost completely dark. As a result, the dashboard 70 gives a good overview of the progress towards the patient's life goals.

The method 200 illustrated in FIG. 4 also includes a patient's feedback 210 that is collected periodically, e.g., every time interval T of system usage. The patient's feedback consists of at least two parts. First, the system usage statistics that is automatically collected by the system based on the patient-care plan interaction. The Care Plan Goals to Life Goals Mapper 32 of the Life Goals-Care Plan Translator 30 will get all this usage statistics. Second, the patient's preferences assessments can be collected via the Life Goal Authoring Tool 31 of the Life Goals-Care Plan Translator 30. Both parts of the patient's feedback 210 can be used to further personalize the care plan, i.e., refine its design and structure. Another refinement can be done by using a set of reference patient profiles and their corresponding care plans as an extra input during the creation of the personalized care plan.

The proposed healthcare system can e.g. be used as a stand-alone telehealth system or as embedded telehealth service in a patient portal such as the personal health book.

In summary, in order to overcome the above mentioned problems, the proposed invention discloses a (preferably two-directional translation) of patient's defined life goals into a personalized care plan. The latter also includes its underlying health goals and (preferably) reverse.

The proposed solution preferably incorporates a feedback loop which takes into account life goals in order to adapt and personalize the care plan. This personalization is based on the patient's input as to what is the major driver for him/her. The patient enters into the system its personal preferences which, via the feedback loop and the actual situation are presented to the patient. The framework of the care plan is therefore based on the input from the patient, which is formatted into an existing template for calculation purpose.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Furthermore, the different embodiments can take the form of a computer program product accessible from a computer usable or computer-readable storage medium providing program code for use by or in connection with a computer or any device or system that executes instructions. For the purposes of this disclosure, a computer usable or computer-readable storage medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer-readable storage medium can be, for example, without limitation, an electronic, magnetic, optical, electromagnetic, infrared, or semiconductor system, or a propagation medium. Non-limiting examples of a computer-readable storage medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer usable or computer-readable storage medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A system for providing a segment based user interface configured to improve user motivation to comply with a care plan, the system comprising:
    a display having different display segments that correspond to different care plan categories of the care plan for the user;
    one or more processors; and
    a non-transitory computer-readable storage medium, wherein the non-transitory computer-readable storage medium includes instructions for execution by the one or more processors, wherein the instructions cause the system to:

for each of the display segments:
determine a dimension for the display segment based on a relative importance of a care plan category that corresponds to the display segment compared to other care plan categories that correspond to other display segments, the dimension of the display segment indicating the relative importance of the care plan category compared to the other care plan categories,
determine a brightness for the display segment based on the user's compliance with the care plan for the care plan category that corresponds to the display segment, and
cause the display segment to be overlaid over at least a portion of a user-selected image for the display segment, wherein a configuration of the overlay is based on the determined dimension and the determined brightness.

2. The system of claim 1, wherein determining the dimension comprises determining a size and/or a shape for the display segment, and wherein causing the display segment to be overlaid comprises causing the display segment to be overlaid over at least a portion of the user-selected image in accordance with the determined size and/or shape.

3. The system of claim 2, wherein the non-transitory computer-readable storage medium further contains instructions for execution by the one or more processors, wherein the instructions cause the system to:
receive life goal information defined by the user; and
determine the relative importance of the care plan category that corresponds to the display segment using a machine learning analysis or cluster analysis of the life goal information.

4. The system of claim 3, wherein determining the relative importance of the care plan category that corresponds to the display segment comprises determining a mapping coefficient that indicates an amount and/or importance of user preference with respect to the life goal information-mapped to the care plan categories.

5. The system of claim 1, wherein the non-transitory computer-readable storage medium further includes instructions for execution by the one or more processors, wherein the instructions cause the system to determine a color for the display segment based on the user's compliance with the care for the care plan category that corresponds to the display segment, wherein the configuration of the overlay is further based on the determined color.

6. The system of claim 1, wherein the non-transitory computer-readable storage medium further includes instructions for execution by the one or more processors, wherein the instructions cause the system to:
visualize the user's compliance with the care plan for each category, wherein the user's compliance with the care plan for each category is indicated through color, the brightness, a bar, and/or a number.

7. The system of claim 1, wherein the non-transitory computer-readable storage medium further contains instructions for execution by the one or more processors, wherein the instructions cause the system to:
receive measurement data related to execution of the care plan by the user, wherein the measurement data are used for determining the user's compliance with the care plan for each category of the care plan.

8. The system of claim 1, wherein the care plan categories include two or more categories of the group of categories comprising physiological, emotional, nutritional, social, spiritual, and/or occupational.

9. The system of claim 8, wherein the care plan category physiological includes one or more of vital signs measurements for detection of worsening symptoms, medication compliance, and/or physical exercises,
wherein the care plan category emotional includes anxiety, depression, happiness, and/or mood,
wherein the care plan category nutritional includes diet, weight, and/or habits, wherein the care plan category social includes relationships, friendships, and/or support network,
wherein the care plan category spiritual includes religious, philosophical, and/or belief system, and
wherein the care plan category occupational includes work, intellect, academia, and/or financial.

10. A method for providing a segment based user interface configured to improve user motivation to comply with a care plan, the method comprising:
displaying different display segments that correspond to different care plan categories of the care plan for the user; and
for each of the display segments:
determining a dimension for the display segment based on a relative importance of a care plan category that corresponds to the display segment compared to other care plan categories that correspond to other display segments, the dimension of the display segment indicating the relative importance of the care plan category compared to the other care plan categories,
determining a brightness for the display segment based on the user's compliance with the care plan for the care plan category that corresponds to the display segment, and
causing the display segment to be overlaid over at least a portion of a
user-selected image for the display segment, wherein a configuration of the overlay is based on the determined dimension and the determined brightness.

11. The system of claim 10, wherein determining the dimension comprises determining a size and/or a shape for the display segment, and wherein causing the display segment to be overlaid comprises causing the display segment to be overlaid over at least a portion of the user-selected image in accordance with the determined size and/or shape.

12. The method of claim 11, further comprising: receiving life goal information defined by the user; and
determining the relative importance of the care plan category that corresponds to the display segment using a machine learning analysis or cluster analysis of the life goal information.

13. The method of claim 12, wherein determining the relative importance of the care plan category that corresponds to the display segment comprises determining a mapping coefficient that indicates an amount and/or importance of user preference with respect to the life goal information mapped to the care plan categories.

14. The method of claim 10, further comprising determining a color for the display segment based on the user's compliance with the care for the care plan category that corresponds to the display segment, wherein the configuration of the overlay is further based on the determined color.

15. The method of claim 10, further comprising visualizing the user's compliance with the care plan for each category, wherein the user's compliance with the care plan for each category is indicated through color, the brightness, a bar, and/or a number.

16. The method of claim 10, further comprising receiving measurement data related to execution of the care plan by the user, wherein the measurement data are used for determining the user's compliance with the care plan for each category of the care plan.

17. The method of claim 10, wherein the care plan categories include two or more categories of the group of categories comprising physiological, emotional, nutritional, social, spiritual, and/or occupational.

18. The method of claim 17, wherein the care plan category physiological includes one or more of vital signs measurements for detection of worsening symptoms, medication compliance, and/or physical exercises,
wherein the care plan category emotional includes anxiety, depression, happiness, and/or mood,
wherein the care plan category nutritional includes diet, weight, and/or habits, wherein the care plan category social includes relationships, friendships,
and/or support network,
wherein the care plan category spiritual includes religious, philosophical, and/or belief system, and
wherein the care plan category occupational includes work, intellect, academia, and/or financial.

19. A computer-readable non-transitory storage medium containing instructions for execution by a processor, wherein the instructions cause the processor to: display different display segments that correspond to different care plan categories of a care plan for a user; and
for each of the display segments:
determine the user's compliance with the care plan for a care plan category that corresponds to the display segment,
determine a dimension characteristic for the display segment based on a relative importance of the care plan category that corresponds to the display segment compared to other care plan categories that correspond to other display segments, the dimension of the display segment indicating the relative importance of the care plan category compared to the other care plan categories,
determine a brightness characteristic for the display segment based on the user's compliance with the care plan for the care plan category that corresponds to the display segment, and
cause the display segment to be overlaid over at least a portion of a user-selected image for the display segment, wherein a configuration of the overlay is based on the determined dimension characteristic and the determined brightness characteristic.

* * * * *